US010744015B2

(12) United States Patent
Chung et al.

(10) Patent No.: US 10,744,015 B2
(45) Date of Patent: Aug. 18, 2020

(54) SLEEVES FOR EXPANDABLE MEDICAL DEVICES

(71) Applicant: W. L. Gore & Associates, Inc., Newark, DE (US)

(72) Inventors: Karl R. Chung, Phoenix, AZ (US); Susan J. Rudes, Phoenix, AZ (US)

(73) Assignee: W. L. Gore & Associates, Inc., Newark, DE (US)

( * ) Notice: Subject to any disclaimer, the term of this patent is extended or adjusted under 35 U.S.C. 154(b) by 146 days.

(21) Appl. No.: 15/678,806

(22) Filed: Aug. 16, 2017

(65) Prior Publication Data

US 2018/0055670 A1    Mar. 1, 2018

Related U.S. Application Data

(60) Provisional application No. 62/379,001, filed on Aug. 24, 2016.

(51) Int. Cl.
| | | |
|---|---|---|
| *A61F 2/82* | (2013.01) | |
| *A61F 2/92* | (2013.01) | |
| *A61F 2/962* | (2013.01) | |
| *A61F 2/97* | (2013.01) | |
| *A61F 2/958* | (2013.01) | |
| *A61F 2/95* | (2013.01) | |
| *A61M 29/02* | (2006.01) | |

(52) U.S. Cl.
CPC ............. *A61F 2/962* (2013.01); *A61F 2/92* (2013.01); *A61F 2/958* (2013.01); *A61F 2/97* (2013.01); *A61F 2002/9517* (2013.01); *A61M 29/02* (2013.01)

(58) Field of Classification Search
CPC ...... A61F 2/97; A61F 2/92; A61F 2002/9511; A61F 2/07; A61F 2/962; A61F 2/966; A61F 2/82; A61F 2002/06
See application file for complete search history.

(56) References Cited

U.S. PATENT DOCUMENTS

| | | | |
|---|---|---|---|
| 3,530,898 A | | 9/1970 | Wilson |
| 4,237,174 A | * | 12/1980 | Lagardere ............... B29C 61/10 428/99 |
| 5,429,118 A | | 7/1995 | Cole |
| 6,203,550 B1 | | 3/2001 | Olson |
| 6,524,335 B1 | | 2/2003 | Hartley et al. |
| 6,733,521 B2 | | 5/2004 | Chobotov et al. |

(Continued)

FOREIGN PATENT DOCUMENTS

| | | |
|---|---|---|
| EP | 1474074 B1 | 4/2004 |
| EP | 1441668 B1 | 1/2008 |

(Continued)

OTHER PUBLICATIONS

International Search Report and Written Opinion from PCT/US2017/047174, dated Oct. 30, 2017, 12 pages.

*Primary Examiner* — Seema Mathew

(57) ABSTRACT

An endoprosthesis constraining sleeve includes a single sheet of material forming at least two folds, and a common bond line constraining the single sheet of material to maintain the at least two folds and to form at least two discrete lumens. A first lumen of the at least two lumens is configured to receive a constrained endoprosthesis therein. A second lumen of the at least two lumens is configured to receive a control feature therethrough.

18 Claims, 9 Drawing Sheets

(56) References Cited

U.S. PATENT DOCUMENTS

| | | |
|---|---|---|
| 6,911,039 B2 | 6/2005 | Shiu |
| 6,974,471 B2 | 12/2005 | Van Schie |
| 7,081,132 B2 | 7/2006 | Cook |
| 7,147,661 B2 | 12/2006 | Chobotov |
| 7,591,832 B2 | 9/2009 | Eversull |
| 7,655,034 B2 | 2/2010 | Mitchell et al. |
| 7,837,724 B2 | 11/2010 | Keeble |
| 7,875,049 B2 | 1/2011 | Eversull |
| 7,938,851 B2 | 5/2011 | Olson |
| 7,976,575 B2 | 7/2011 | Hartley |
| 8,167,927 B2 | 5/2012 | Chobotov |
| 8,241,346 B2 | 8/2012 | Chobotov |
| 8,257,431 B2 | 9/2012 | Henderson |
| 8,262,671 B2 | 9/2012 | Osypka |
| 8,328,861 B2 | 12/2012 | Martin |
| 8,361,135 B2 | 1/2013 | Dittman |
| 8,480,725 B2 | 7/2013 | Rasmussen |
| 8,968,384 B2 | 3/2015 | Pearson |
| 9,060,895 B2 | 6/2015 | Hartley |
| 9,132,025 B2 | 9/2015 | Aristizabal |
| 9,254,204 B2 | 2/2016 | Roeder |
| 9,308,349 B2 | 4/2016 | Rezac |
| 9,498,361 B2 | 11/2016 | Nevins |
| 9,585,743 B2 | 3/2017 | Cartledge |
| 9,585,774 B2 | 3/2017 | Aristizabal |
| 9,681,968 B2 | 6/2017 | Goetz |
| 9,700,701 B2 | 7/2017 | Benjamin |
| 9,782,284 B2 | 10/2017 | Hartley |
| 9,937,070 B2 | 4/2018 | Skelton |
| 9,987,155 B1 * | 6/2018 | Sondreaal ............... A61F 2/962 |
| 2002/0029077 A1 * | 3/2002 | Leopold ................... A61F 2/07 |
| | | 623/1.11 |
| 2002/0103527 A1 | 8/2002 | Kocur et al. |
| 2006/0217755 A1 * | 9/2006 | Eversull ............. A61B 17/3439 |
| | | 606/191 |
| 2007/0225797 A1 | 9/2007 | Krivoruhko |
| 2010/0010535 A1 | 1/2010 | Mujkanovic |
| 2010/0049294 A1 | 2/2010 | Zukowski |
| 2010/0211156 A1 | 8/2010 | Linder |
| 2012/0130475 A1 * | 5/2012 | Shaw ........................ A61F 2/97 |
| | | 623/1.12 |
| 2012/0296360 A1 * | 11/2012 | Norris ....................... A61F 2/97 |
| | | 606/191 |
| 2013/0018450 A1 | 1/2013 | Hunt |
| 2013/0123896 A1 * | 5/2013 | Bloss ....................... A61F 2/97 |
| | | 623/1.11 |
| 2013/0158647 A1 * | 6/2013 | Norris ....................... A61F 2/97 |
| | | 623/1.12 |
| 2014/0106951 A1 * | 4/2014 | Brandon .................. A61F 2/97 |
| | | 493/384 |
| 2014/0120287 A1 * | 5/2014 | Jacoby .................... B29C 53/56 |
| | | 428/36.91 |
| 2017/0172724 A1 | 6/2017 | Cartledge |
| 2017/0281382 A1 | 10/2017 | Lostetter |
| 2018/0036011 A1 * | 2/2018 | Lehnhardt ........ A61B 17/12118 |

FOREIGN PATENT DOCUMENTS

| | | |
|---|---|---|
| EP | 1915113 B1 | 3/2010 |
| EP | 1358903 B1 | 2/2011 |
| EP | 2749251 B1 | 7/2016 |
| EP | 2956198 B1 | 11/2017 |
| JP | 2005-503184 A | 2/2005 |
| WO | WO-2001028453 A2 | 4/2001 |
| WO | 02/60351 A1 | 8/2002 |
| WO | WO-2003090834 A2 | 11/2003 |
| WO | WO-2012065080 A2 | 5/2012 |

* cited by examiner

SLEEVES FOR EXPANDABLE MEDICAL DEVICES

CROSS-REFERENCE TO RELATED APPLICATION

This application claims the benefit of U.S. Provisional Application No. 62/379,001, filed Aug. 24, 2016, which is herein incorporated by reference in its entirety.

FIELD

The present disclosure relates generally to the transcatheter delivery and remote deployment of implantable medical devices.

BACKGROUND

Endoluminal devices used to treat a treatment area of the vasculature of a patient are typically delivered via a delivery system including a catheter. Such endoluminal devices may comprise, for example, expandable implants. Expandable endoluminal devices can be comprised of a graft or a stent component with or without a graft covering over the stent interstices. They can be designed to expand when a restraint, such as a sleeve is removed or be balloon-expanded from a delivery diameter to a pre-determined functional diameter.

SUMMARY OF THE DISCLOSURE

This disclosure is generally directed to flexible sleeves formed from a single sheet of material including a first lumen configured to receive a constrained implantable medical device, such as an endoprosthesis, and a second lumen configured to receive at least one control feature, such as a deployment feature and/or a steering member.

In one variation, an endoprosthesis constraining sleeve includes a single sheet of material forming at least two folds, and a common bond line constraining the single sheet of material to maintain the at least two folds and to form at least two discrete lumens. A first lumen of the at least two lumens is configured to receive a constrained endoprosthesis therein. A second lumen of the at least two lumens is configured to receive a control feature therethrough.

In some examples, the control feature includes one or more of a group consisting of: a deployment feature, and a steering member.

In the same or different examples, the common bond line includes at least one of: a thermal bond, and a stitch line.

In the same or different examples, the first lumen is formed from a single layer of the single sheet of material. In some of such examples, the second lumen is formed from two layers of the single sheet of material. In other of such examples, the second lumen is formed from a single layer of the single sheet of material.

In the same or different examples, the single sheet of material includes a first side and a second side, and an interior surface of the first lumen is formed by the first side of the single sheet of material, and an interior surface of the second lumen is formed by the first side of the single sheet of material.

In the same or different examples, the single sheet of material includes a first side and a second side, an interior surface of the first lumen is formed by the first side of the single sheet of material, and an interior surface of the second lumen is formed by the second side of the single sheet of material. In some of such examples, the second lumen is formed from two layers of the single sheet of material. In some of such examples, the second lumen is within the first lumen. In some of such examples, a first fold of the at least two bends the first side of the single sheet of material back on itself towards the common bond line to form the first lumen, and a second fold of the at least two bends the second side of the single sheet of material back on itself towards the common bond line to form the second lumen.

In the same or different examples, the at least two folds includes at least three folds, the at least two discrete lumens includes at least three discrete lumens, and the common bond line constrains the single sheet of material to maintain the at least three folds and to form the at least three discrete lumens.

In the same or different examples, the common bond line is generally parallel with a longitudinal axis of the constrained endoprosthesis.

In the same or different examples, the first lumen is configured to constrain the endoprosthesis to an intermediate configuration.

In the same or different examples, the single sheet of material includes an expanded polytetrafluoroethylene (ePTFE) base layer. In some of such examples, the single sheet of material includes a thermoplastic coating on one side of the ePTFE base layer.

In the same or different examples, the single sheet of material includes fluorinated ethylene propylene (FEP) layer.

In the same or different examples, the endoprosthesis is a stent graft.

In another variation, an endoprosthesis delivery system includes: a primary sleeve, a secondary sleeve within the primary sleeve, an expandable endoprosthesis within the primary sleeve and the secondary sleeve, the primary sleeve constraining the expandable endoprosthesis to a collapsed configuration, and a control feature. The secondary sleeve is formed from a single sheet of material forming at least two folds, the secondary sleeve including a common bond line constraining the single sheet of material to maintain the at least two folds and to form at least two discrete lumens. The expandable endoprosthesis is constrained within a first lumen of the at least two lumens. The control feature extends within a second lumen of the at least two lumens.

In some examples, the first lumen is configured to constrain the endoprosthesis to an intermediate configuration following the release of the expandable endoprosthesis from the primary sleeve, the intermediate configuration being larger than the collapsed configuration and smaller than a fully deployed configuration.

In the same or different examples, control feature is a deployment feature configured to release the expandable endoprosthesis from the primary sleeve.

In the same or different examples, the endoprosthesis delivery system further includes a secondary deployment feature configured to release the expandable endoprosthesis from the first lumen of secondary sleeve to allow expansion from the intermediate configuration to the fully deployed configuration. In some of such examples, the common bond line includes a stitch line, and the secondary deployment feature is a deployment line configured to release the stitch line.

BRIEF DESCRIPTION OF THE DRAWINGS

The accompanying drawings are included to provide a further understanding of the disclosure and are incorporated in and constitute a part of this specification, illustrate examples of the disclosure, and together with the description serve to explain the principles of the disclosure, wherein.

DETAILED DESCRIPTION

Various examples of the present disclosure are directed to flexible sleeves including a first lumen configured to receive a constrained endoprosthesis therein, and a second lumen configured to receive a delivery system component, such as at least one control feature (e.g., a deployment feature and/or a steering member). Providing a separate lumen for a delivery system component may improve the reliability of the system (e.g., by limiting contact between components of a delivery system including the sleeve), may reduce undesirable contact between a delivery system component and a vessel wall thereby reducing a risk of trauma to the vessel (e.g., by limiting contact between components of a delivery, such as a steering wire, and the vessel wall), and may simplify the manufacture of such delivery systems, and achieve additional or alternative advantages.

In some of such examples, one or more flexible sleeves may further be configured to releasably constrain an expandable implant, such as an expandable endoluminal stent graft, toward a dimension suitable for endoluminal delivery of the implant to a treatment site, such as a vascular member in a patient's body. The one or more flexible sleeves may further constrain the implant to an intermediate outer peripheral dimension that is larger than the dimension suitable for endoluminal delivery but smaller than an unconstrained or fully deployed outer peripheral dimension. Controlled expansion to such an intermediate outer peripheral dimension may facilitate selective axial and/or rotational positioning or other manipulation of the implant at the treatment site prior to full deployment and expansion of the implant.

Figure 1:
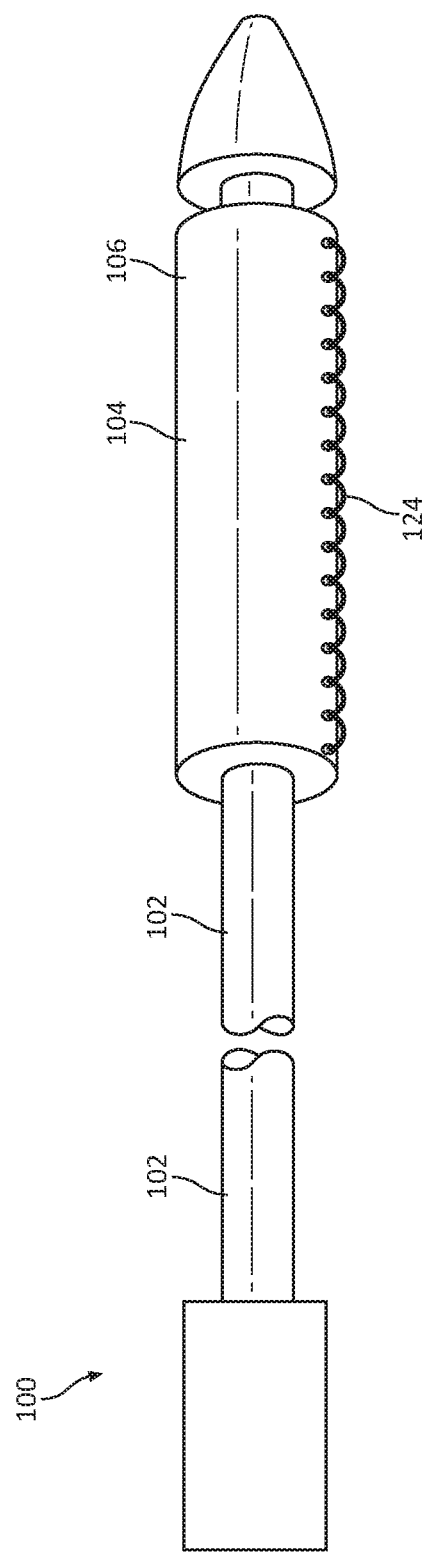
FIG. 1 illustrates a side view of a delivery system for an expandable implant.

Example endoprosthesis constraining sleeves including at least two lumens formed from a single sheet of material are described with respect to FIGS. 3A-6E. FIGS. 1-2B illustrate perspective views of delivery systems having constraining sleeves such as those described in further detail with respect to FIGS. 3A-6E.

With initial reference to FIG. 1, a delivery system 100 in accordance with the present disclosure comprises an expandable implant 106. Expandable implant 106 can comprise any endoluminal device suitable for delivery to the treatment area of a vasculature. Such devices may include, for example, stents, grafts, and stent grafts. Thus, expandable implant 106 can include one or more stent components with one or more associated graft members disposed over and/or under the stent, which can dilate from a delivery diameter, through a range of larger intermediary diameters, and toward a maximal, pre-determined functional diameter.

In various examples, expandable implant 106 comprises one or more stent components made of nitinol and a graft member made of ePTFE. However, and as discussed below, any suitable combination of stent component(s) and graft member(s) is within the scope of the present disclosure.

Stent components can have various configurations such as, for example, rings, cut tubes, wound wires (or ribbons) or flat patterned sheets rolled into a tubular form. Stent components can be formed from metallic, polymeric or natural materials and can comprise conventional medical grade materials such as nylon, polyacrylamide, polycarbonate, polyethylene, polyformaldehyde, polymethylmethacrylate, polypropylene, polytetrafluoroethylene, polytrifluorochlorethylene, polyvinylchloride, polyurethane, elastomeric organosilicon polymers; metals such as stainless steels, cobalt-chromium alloys and nitinol and biologically derived materials such as bovine arteries/veins, pericardium and collagen. Stent components can also comprise bioresorbable materials such as poly(amino acids), poly(anhydrides), poly (caprolactones), poly(lactic/glycolic acid) polymers, poly (hydroxybutyrates) and poly(orthoesters). Any expandable stent component configuration which can be delivered by a catheter is in accordance with the present disclosure.

Moreover, potential materials for graft members include, for example, expanded polytetrafluoroethylene (ePTFE), polyester, polyurethane, fluoropolymers, such as perfouorelastomers and the like, polytetrafluoroethylene, silicones, urethanes, ultra-high molecular weight polyethylene, aramid fibers, and combinations thereof. Other examples for a graft member material can include high strength polymer fibers such as ultra-high molecular weight polyethylene fibers (e.g., Spectra®, Dyneema Purity®, etc.) or aramid fibers (e.g., Technora®, etc.). The graft member may include a bioactive agent. In one example, an ePTFE graft includes a carbon component along a blood contacting surface thereof. Any graft member that can be delivered by a catheter is in accordance with the present disclosure.

In various examples, a stent component and/or graft member can comprise a therapeutic coating. In these examples, the interior and/or exterior of the stent component and/or graft member can be coated with, for example, a CD34 antigen. Additionally, any number of drugs or therapeutic agents can be used to coat the graft member, including, for example heparin, sirolimus, paclitaxel, everolimus, ABT-578, mycophenolic acid, tacrolimus, estradiol, oxygen free radical scavenger, biolimus A9, anti-CD34 antibodies, PDGF receptor blockers, MMP-1 receptor blockers, VEGF, G-CSF, HMG-CoA reductase inhibitors, stimulators of iNOS and eNOS, ACE inhibitors, ARBs, doxycycline, and thalidomide, among others.

In various examples, expandable implant 106 can comprise a radially collapsed configuration suitable for delivery to the treatment area of the vasculature of a patient. Expandable implant 106 can be constrained toward a radially collapsed configuration and releasably mounted onto a delivery device such as catheter shaft 102. The diameter of the expandable implant 106 in the collapsed configuration is small enough for the implant to be delivered through the vasculature to the treatment area. In various examples, the diameter of the collapsed configuration is small enough to minimize the crossing profile of delivery system 100 and reduce or prevent tissue damage to the patient. In the collapsed configuration, the expandable implant 106 can be guided by catheter shaft 102 through the vasculature.

In various examples, expandable implant 106 can comprise a radially expanded configuration suitable for implanting the device in the treatment area of a patient's vasculature. In the expanded configuration, the diameter of expandable implant 106 can be approximately the same as the vessel to be repaired. In other examples, the diameter of expandable implant 106 in the expanded configuration can be slightly larger than the vessel to be treated to provide a traction fit within the vessel.

In various examples, expandable implant 106 can comprise a self-expandable device, such as a self-expandable stent graft. Such devices dilate from a radially collapsed configuration to a radially expanded configuration when unconstrained. In other examples, expandable implant 106 can comprise a device that is expanded with the assistance of a secondary device such as, for example, a balloon. In yet other examples, delivery system 100 can comprise a plurality of expandable implants 106. The use of a delivery system with any number of expandable implants is within the scope of the present disclosure.

Various medical devices in accordance with the disclosure comprise a sleeve or multiple sleeves. The sleeve or sleeves may constrain an expandable implant device in a collapsed configuration for endoluminal delivery of the implant to a treatment portion of the vasculature of a patient. For the purposes of the disclosure, the term "constrain" may mean (i) to limit the expansion, either through self-expansion or assisted by a device, of the diameter of an expandable implant or (ii) to cover or surround but not otherwise constrain an expandable implant (e.g., for storage or biocompatibility reasons and/or to provide protection to the expandable implant and/or the vasculature). Delivery system 100, for example, comprises a sleeve 104 which surrounds and constrains expandable implant 106 toward a reduced diameter or collapsed configuration.

After deployment, the sleeve or sleeves can be removed in order to allow the expandable implant to expand toward a functional diameter and achieve a desired therapeutic outcome. Alternatively, the sleeve or sleeves can remain coupled to the implant or otherwise implanted while not interfering with the expandable implant.

In various examples, an expandable implant is constrained by a single sleeve which circumferentially surrounds the expandable implant. For example, with reference to FIG. 2B, delivery system 200 comprises a sleeve 204. In various examples, sleeve 204 circumferentially surrounds expandable implant 206 and constrains it toward a collapsed configuration, in which the diameter is less than the diameter of an unconstrained or otherwise deployed implant. For example, sleeve 204 may constrain expandable implant 206 toward a collapsed configuration for delivery within the vasculature. In this example, expandable implant 206 represents an expandable endoprosthesis, such as a stent, a graft, or a stent graft.

In other examples, an expandable implant is constrained by a plurality of sleeves which circumferentially surround the expandable implant, which allow the expandable implant to be deployed and held at intermediate configurations larger than the collapsed configuration and smaller than the deployed configuration. The plurality of sleeves can comprise at least two sleeves which circumferentially surround each other.

In various examples, sleeves can be tubular and serve to constrain an expandable implant. In such configurations, sleeves are formed from a sheet of one or more materials wrapped or folded about the expandable implant. While the illustrative examples herein are described as comprising one or more tubular sleeves, sleeves of any non-tubular shape that corresponds to an underlying expandable implant or that are otherwise appropriately shaped for a given application are also within the scope of the present disclosure.

In various examples, sleeves are formed by wrapping or folding the sheet of material(s) such that two parallel edges of the sheet are substantially aligned. Said alignment may or may not be parallel to or coaxial with the catheter shaft of a delivery system. In various examples, a single coupling member can be used to constrain the diameter of two or more sleeve lumens, e.g., as illustrated in further detail with respect to FIGS. 3A-6E.

In various examples, the edges of the sheet of material(s) do not contact each other. In other examples, the edges of the sheet of material(s) do contact each other and are coupled with a coupling member (as described below), a thermal bond, an adhesive, or the like. In various other examples, the edges of the sheet of material(s) are aligned so that the edges of the same side of the sheet or sheets (e.g., the front or back of the sheet) are in contact with each other. In still other examples, the edges of opposite sides of the sheet of material(s) are in contact with each other, such that the edges overlap each other, such that a portion of one side of the sheet is in contact with a portion of the other side. Said another way, the front of the sheet may overlap the rear of the sheet, or vice versa.

The sheet of material(s) used to form the sleeve(s) can comprise a series of openings, such that the openings extend from one edge of the sheet to the other. In such configurations, a coupling member can be woven or stitched through the series of openings in the sheet of material(s), securing each of the two edges together and forming a tube. For example, in FIG. 1, coupling member 124 secures the edges of sleeve 104 such that sleeve 104 maintains expandable implant 106 toward a reduced diameter or outer peripheral dimension suitable for endoluminal delivery.

In various examples, the coupling member can comprise a woven fiber. In other examples, the coupling member can comprise a monofilament fiber. Any type of string, cord, thread, fiber, or wire which is capable of maintaining a sleeve in a tubular shape is within the scope of the present disclosure.

Once a suitable expandable implant is in a collapsed configuration, the expandable implant can be deployed within the vasculature of a patient. An expandable implant in a collapsed configuration can be introduced to a vasculature and directed by a delivery system to a treatment area of the vasculature.

When the expandable implant is in position within the vasculature, the coupling member or members can be disengaged from the sleeve or sleeves from outside of the body of the patient, which allows the sleeve(s) to open and the expandable implant to expand. The coupling member or members can be disengaged from the sleeve or sleeves by a mechanical mechanism operated from outside of the body of the patient. For example, the member or members can be disengaged by applying sufficient tension to the member or members. In another example, a translatable element can be attached to the coupling member or members outside of the body. Displacement of the translatable elements, such as rotation of a dial or rotational member or translation of a handle or knob, may provide sufficient tension to displace and disengage the coupling member or members.

In various examples, disengaging a single coupling member which closes a single sleeve of a set of concentric sleeves allows the expandable device to be expanded toward a larger diameter or outer peripheral dimension. A primary sleeve may constrain the expandable device in a fully-collapsed configuration whereas a secondary sleeve may constrain the expandable device in an intermediate configuration once the expandable device is released from the primary sleeve.

In the intermediate configuration, the diameter of the expandable implant is constrained in a diameter smaller than the expanded configuration and larger than the collapsed configuration. For example, the diameter of the expandable device in the intermediate configuration can be about 70% of the diameter of the expandable device in the expanded configuration. However, any diameter of the intermediate configuration which is less than the diameter of the expanded configuration and larger than the collapsed configuration is contemplated by this disclosure.

In such examples, the expandable implant can be expanded from the collapsed configuration toward the intermediate configuration once the implant has been delivered near the treatment area of the vasculature of a patient. The intermediate configuration may, among other things, assist in properly orienting and locating the expandable implant within the treatment area of the vasculature. In addition, sleeves including at least two lumens that are as large or larger than the expanded configuration are also contemplated by this disclosure. Such sleeves may allow full deployment of an endoprosthesis within one lumen with one or more control features being located within one or more other lumens. Such control features are separated from the endoprosthesis even under full expansion, thereby still providing advantages of having at least two lumens as described in this disclosure.

In various examples, an expandable implant can be concentrically surrounded by two sleeves having different diameters. In such configurations, a primary sleeve constrains the expandable implant toward the collapsed configuration. Once the collapsed configuration sleeve is opened, a secondary sleeve constrains the expandable implant toward the intermediate configuration. As discussed above, the expandable implant can be self-expanding, or the implant can be expanded by a device, such as a balloon.

Figure 2A:
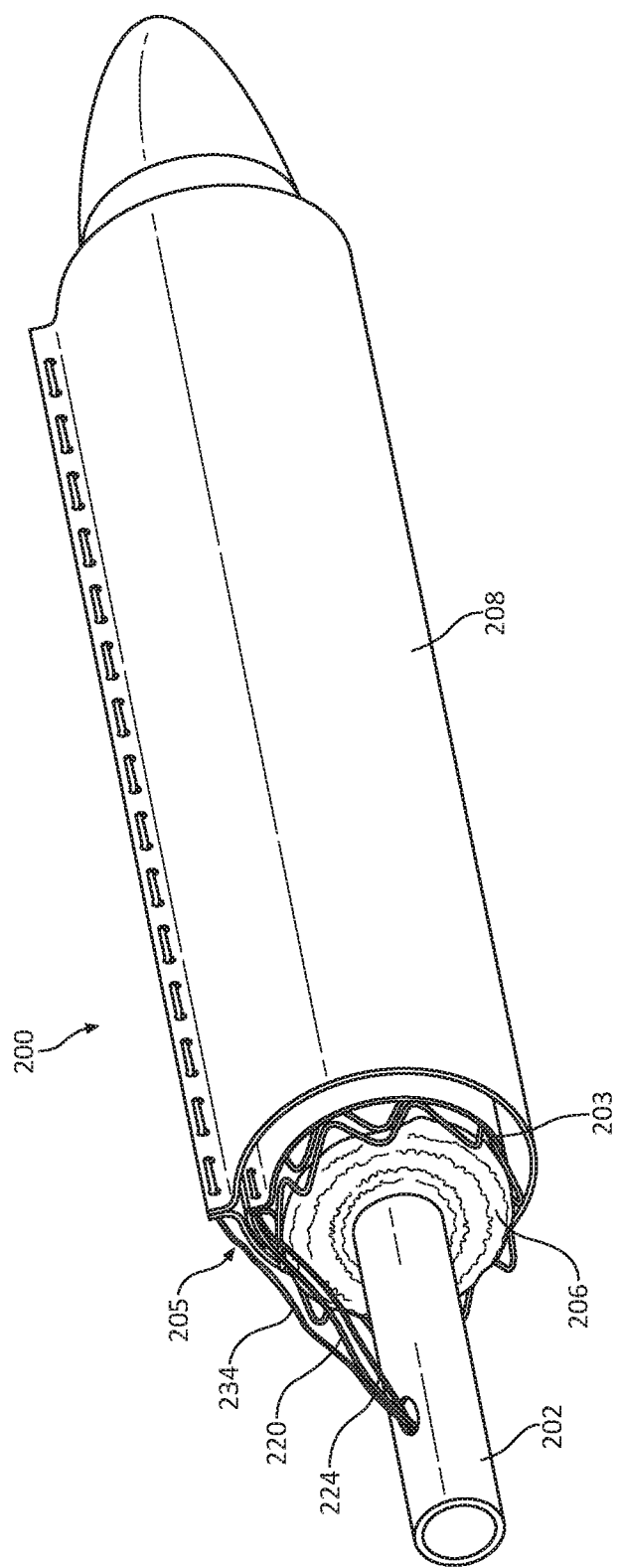
FIGS. 2A and 2B illustrate perspective views of delivery systems for expandable implants, the delivery systems including constraining sleeves with at least two lumens.
Figure 2B:
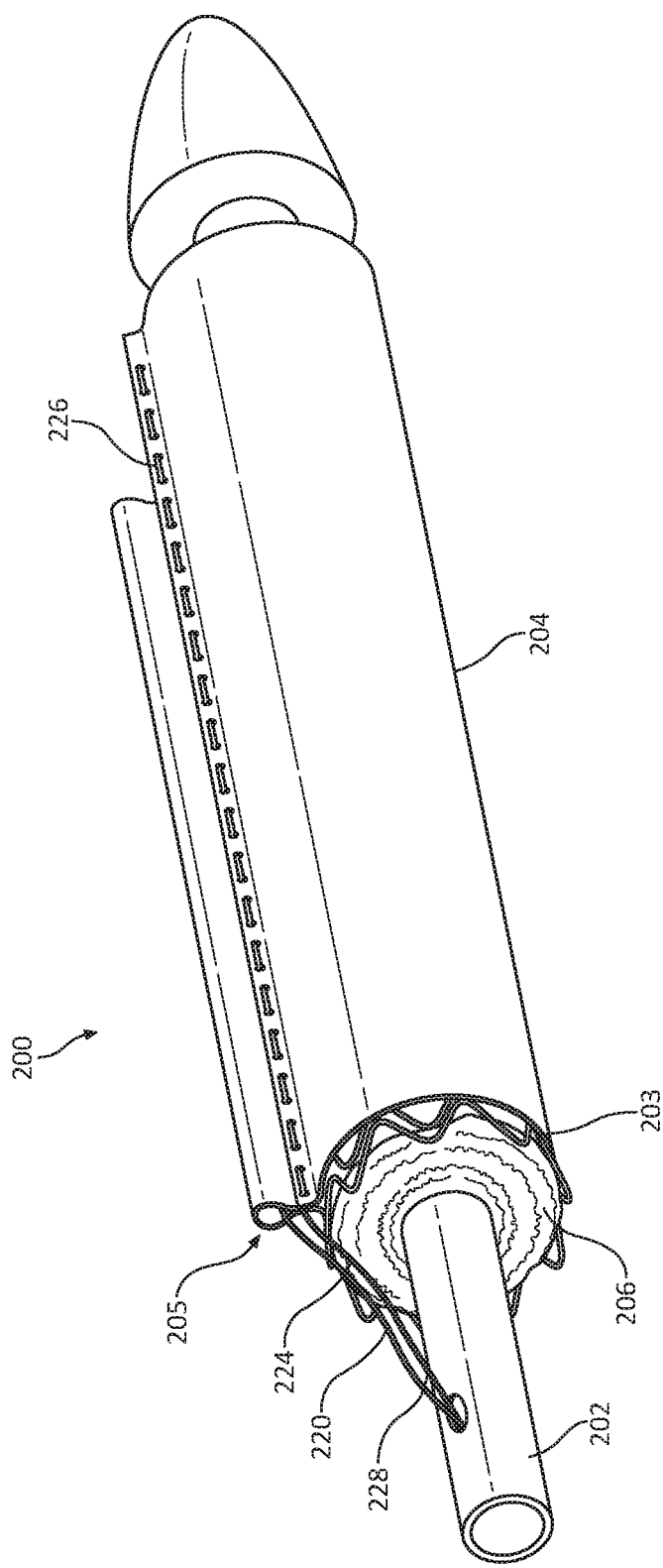

For example, with reference to FIG. 2A, a delivery system 200 comprises an expandable implant 206, sleeve 208, and secondary sleeve 204. Secondary sleeve 204 constrains expandable implant 206 toward an intermediate configuration. Secondary sleeve 204 is held in position around expandable implant 206 by secondary coupling member 224.

Delivery system 200 further comprises a primary sleeve 208, which constrains expandable implant 206 toward a collapsed configuration for delivery to the vasculature of a patient. Primary sleeve 208 is held in position around expandable implant 206 by primary coupling member 234. Coupling member 234 represents a deployment feature as pulling on a proximal end of coupling member 234 may release coupling member 234 from sleeve 208 to deploy expandable implant 206. For example, during an implantation procedure, once expandable implant 206 is sufficiently close to the treatment area of the vasculature, primary coupling member 234 is disengaged from primary sleeve 208, which releases primary sleeve 208 and allows expanded implant 206 to expand toward a larger diameter.

With reference to FIG. 2B, after primary sleeve 208 has been released, first lumen 203 of secondary sleeve 204 constrains the expandable implant 206 toward the intermediate configuration. In the intermediate configuration, expandable implant 206 can be oriented and adjusted (e.g., by bending and torsional rotation) to a desired location within the treatment area of the vasculature.

Although a number of specific configurations of constraining members (for example, primary and secondary members) and sleeves (for example, primary and secondary sleeves) have been discussed, the use of any number and/or configuration of constraining members and any number of sleeves is within the scope of the present disclosure.

In some particular examples, expandable implant 206 may be an expandable endoprosthesis used to treat abdominal aortic aneurisms such that expandable implant 206 is configured to seal-off the weakened wall of the aorta. Delivery to the treatment site may occur via the iliac or femoral arteries in the thigh. The bends and angles of such vasculatures may cause difficulties that are mitigated by the design of secondary sleeve 204.

For example, in the illustrated example, secondary sleeve 204 further includes a second lumen 205, which is configured to receive at least one delivery system component, such as at least one control feature (e.g., a deployment feature and/or a steering member). Examples sleeves with at least two lumens are illustrated in further detail with respect to FIGS. 3A-6E. In different examples, the control feature within a second lumen may be a steering member, such as steering line 220 or a guidewire, a deployment feature, such as coupling member 224 and/or coupling member 234, or another control feature. Providing a separate lumen for a control feature may improve the reliability of the control feature by limiting contact with a constrained endoprosthesis or other components of a delivery system including the sleeve and/or simplify the manufacture of a delivery system including the sleeve by separating the control feature from the constrained endoprosthesis and, optionally from other components of the delivery system, such as a stich line of the sleeve.

Secondary sleeve 204 is formed from a single sheet of material forming at least two folds, and includes a common bond line constraining the single sheet of material to maintain the at least two folds and to form at least two discrete lumens, including first lumen 203 and second lumen 205. In the disclosed example, coupling member 224 forms a stitch line 226, which represents the common bond line. The distal end coupling member 224 represents a deployment line 228 configured to release stitch line 226. In other examples, the common bond line may represent a thermal bond, an adhesive bond or other bond.

In some particular examples, the single sheet of material forming secondary sleeve 204 includes an ePTFE base layer. In the same or different examples, the single sheet of material forming secondary sleeve 204 may include a thermoplastic coating on one or both sides of the base layer, such as a fluorinated ethylene propylene (FEP) layer.

In various examples, the delivery system further comprises a steering line. In such configurations, tension can be applied to the steering line to displace the steering line and bend the expandable implant. Bending the expandable implant may, among other things, assist in travelling through curved or tortuous regions of vasculature. Bending the expandable implant may also allow the implant to conform to curvatures in the vasculature of a patient, such as curvatures occurring during implantation to correct an abdominal aortic aneurism.

With reference to FIGS. 2A-2B, steering line 220, an example steering member, passes from the outside of the body of a patient, through catheter shaft 202, through second lumen 205 of secondary sleeve 204, and is releasably coupled to expandable implant 206. In such configurations, steering line 220 can be threaded through expandable implant 206 such that tension applied to steering line 220 from outside of the body of the patient causes expandable implant 206 to bend in a desired manner. For example, a suitable steering line is disclosed by U.S. Pat. No. 9,375,308, titled, "EXTERNAL STEERABLE FIBER FOR USE IN ENDOLUMINAL DEPLOYMENT OF EXPANDABLE DEVICES," the entire contents of which are incorporated by reference herein.

In various examples, steering line 220 can comprise metallic, polymeric or natural materials and can comprise conventional medical grade materials such as nylon, polyacrylamide, polycarbonate, polyethylene, polyformaldehyde, polymethylmethacrylate, polypropylene, polytetrafluoroethylene, polytrifluorochlorethylene, polyvinylchloride, polyurethane, elastomeric organosilicon polymers; metals such as stainless steels, cobalt-chromium alloys and nitinol. Elongated members or lock wires can also be formed from high strength polymer fibers such as ultrahigh molecular weight polyethylene fibers (e.g., Spectra®, Dyneema Purity®, etc.) or aramid fibers (e.g., Technora®, etc.).

In various examples, expandable implant 206 may comprise a fenestratable portion. In such configurations, expandable implant 206 may include a frangible material which may be fenestrated by an endoluminal tool after expandable implant 206 has been partially or completely implanted in the vasculature of a patient. Once fenestrated, fenestratable portion may be used, for example, to install branching stent grafts to expandable implant 206. Side branch fenestrations allow for branching devices, such as branching stent grafts, to be connected to and in with communication expandable implant 206. Such fenestrations and branching stent grafts may facilitate conforming expandable implant 206 and additional branching stent grafts to the anatomy of a patient, such as iliac arteries and associated vascular branches.

Example endoprosthesis constraining sleeves including at least two lumens formed from a single sheet of material are described with respect to FIGS. 3A-6E. These example endoprosthesis constraining sleeves are each suitable for use as secondary sleeve 204, as are numerous other variations not specifically illustrated.

Figure 3A:
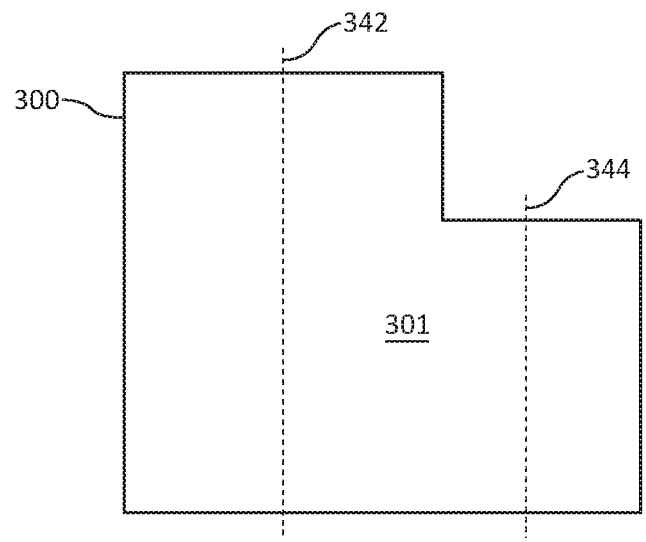
FIGS. 3A-3C illustrate example techniques for forming an endoprosthesis constraining sleeve including two lumens from a single sheet of material with two folds and a common bond line.
Figure 3B:
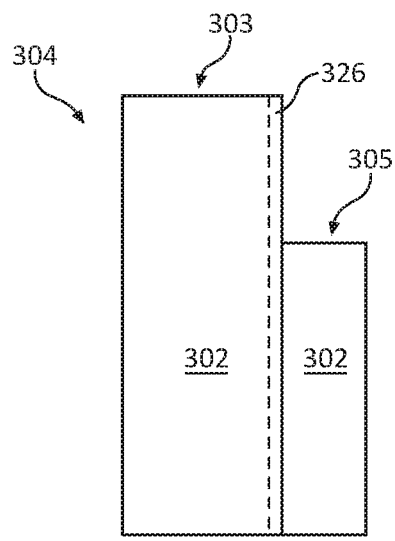
Figure 3C:
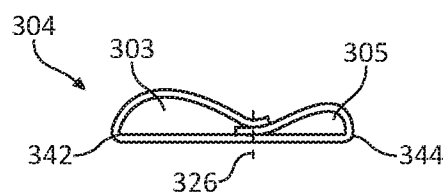

FIGS. 3A-3C illustrate techniques for forming endoprosthesis constraining sleeve 304, which includes two lumens 303, 305. Endoprosthesis constraining sleeve 304 is formed from a single sheet of material 300 (FIG. 3A) with two folds 342, 344 and a common bond line 326. Endoprosthesis constraining sleeve 304 may be used as secondary sleeve 204 within delivery system 200, as the only constraining sleeve within another delivery system, or with any medical assembly in which it is useful to provide at least two adjacent lumens.

The single sheet of material 300 includes a first side 301 and a second side 302. In some examples, single sheet of material 300 may include an exposed ePTFE layer on second side 302 with an exposed thermoplastic layer, such as an FEP layer on first side 301.

To form endoprosthesis constraining sleeve 304 from the single sheet of material 300, fold 342 is made to form lumen 303, and fold 344 is made to form lumen 305. Folds 342, 344 each bends side 301 back on itself towards common bond line 326 to form lumens 303, 305.

Lumen 303 may be configured to receive a constrained implantable medical device, such as an endoprosthesis, and lumen 305 may be configured to receive at least one control feature, such as a deployment feature and/or a steering member. Lumen 305 is optionally shorted than lumen 303.

After folding, common bond line 326, which may, for example, represent a stich line or a thermal bond, maintains folds 342, 344 to form lumens 303, 305. Common bond line 326 may be generally parallel with a longitudinal axis of an endoprosthesis constrained within one of lumens 303, 305.

FIG. 3B illustrates a top view of endoprosthesis constraining sleeve 304, and FIG. 3C illustrates a side view of endoprosthesis constraining sleeve 304. As best illustrated in FIG. 3C, lumens 303, 305 are each formed from a single layer of the single sheet of material 300. The interior surfaces of lumens 303, 305 are each formed from side 301 of the single sheet of material 300. In other examples, the orientation of the single sheet of material 300 could be reversed such that interior surfaces of lumens 303, 305 are each formed from side 302 of the single sheet of material 300.

Figure 4A:
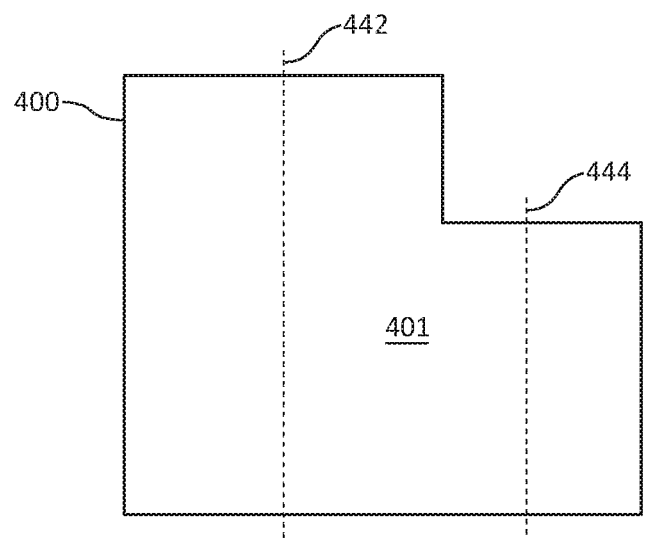
FIGS. 4A-4C illustrate additional example techniques for forming an endoprosthesis constraining sleeve including two lumens from a single sheet of material with two folds and a common bond line.
Figure 4B:
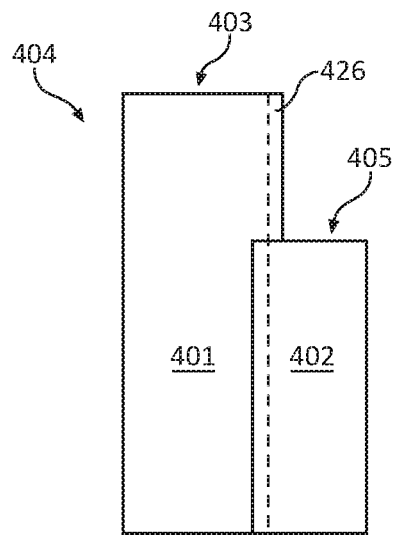
Figure 4C:
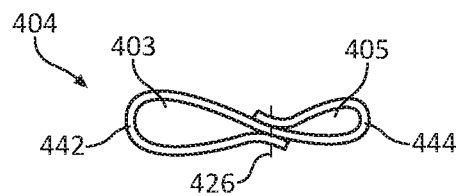

FIGS. 4A-4C illustrate techniques for forming endoprosthesis constraining sleeve 404, which includes two lumens 403, 405. Endoprosthesis constraining sleeve 404 is formed from a single sheet of material 400 (FIG. 4A) with two folds 442, 444 and a common bond line 426. Endoprosthesis constraining sleeve 404 may be used as secondary sleeve 204 within delivery system 200, as the only constraining sleeve within another delivery system, or with any medical assembly in which it is useful to provide at least two adjacent lumens.

The single sheet of material 400 includes a first side 401 and a second side 402. In some examples, single sheet of material 400 may include an exposed ePTFE layer on second side 402 with an exposed thermoplastic layer, such as an FEP layer on first side 401.

To form endoprosthesis constraining sleeve 404 from the single sheet of material 400, fold 442 is made to form lumen 403, and fold 444 is made to form lumen 405. Fold 442 bends side 402 back on itself towards common bond line 426 to form lumen 403, whereas fold 444 bends side 401 back on itself towards common bond line 426 to form lumen 405.

Lumen 403 may be configured to receive a constrained implantable medical device, such as an endoprosthesis, and lumen 405 may be configured to receive at least one control feature, such as a deployment feature and/or a steering member. Lumen 405 is optionally shorted than lumen 403. After folding, common bond line 426, which may, for example, represent a stich line or a thermal bond, maintains folds 442, 444 to form lumens 403, 405. Common bond line 426 may be generally parallel with a longitudinal axis of an endoprosthesis constrained within one of lumens 403, 405.

FIG. 4B illustrates a top view of endoprosthesis constraining sleeve 404, and FIG. 4C illustrates a side view of endoprosthesis constraining sleeve 404. As best illustrated in FIG. 4C, lumens 403, 405 are each formed from a single layer of the single sheet of material 400. The interior surfaces of lumen 403 are formed from side 402 of the single sheet of material 400, whereas the interior surfaces of lumen 403 are formed from side 401 of the single sheet of material 400. In other examples, the orientation of the single sheet of material 400 could be reversed such interior surfaces of lumen 403 are formed from side 401 of the single sheet of material 400, and the interior surfaces of lumen 403 are formed from side 402 of the single sheet of material 400.

FIGS. 5A-5F illustrate techniques for forming endoprosthesis constraining sleeve 504, which includes two lumens 503, 505. Endoprosthesis constraining sleeve 504 is formed from a single sheet of material 500 (FIG. 5A) with two folds 542, 544 and a common bond line 526. Endoprosthesis constraining sleeve 504 may be used as secondary sleeve 204 within delivery system 200, as the only constraining sleeve within another delivery system, or with any medical assembly in which it is useful to provide at least two adjacent lumens.

The single sheet of material 500 includes a first side 501 and a second side 502. In some examples, the single sheet of material 500 may include an exposed ePTFE layer on second side 502 with an exposed thermoplastic layer, such as an FEP layer on first side 501.

Figure 5A:
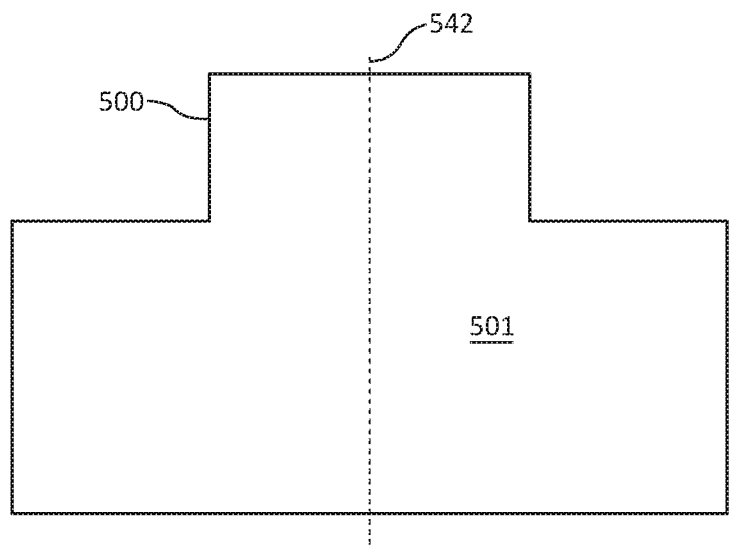
FIGS. 5A-5F illustrate further example techniques for forming an endoprosthesis constraining sleeve including two lumens from a single sheet of material with two folds and a common bond line.
Figure 5B:
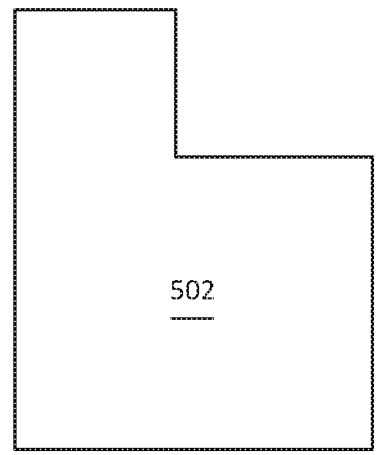
Figure 5C:
Figure 5D:
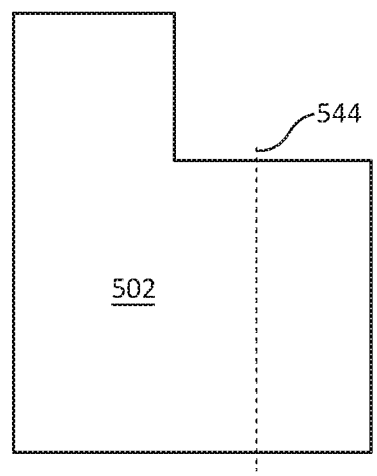
Figure 5E:
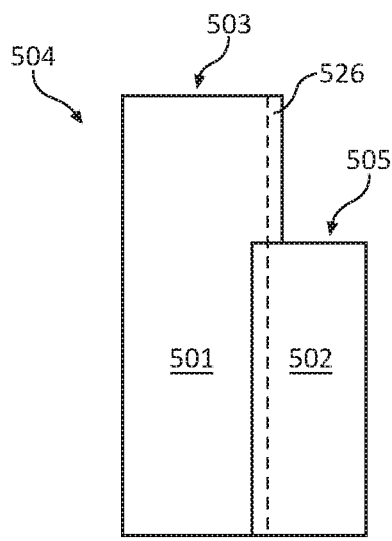

As shown in FIGS. 5B and 5C, to form endoprosthesis constraining sleeve 504, fold 542 bends side 501 back on itself to fold the single sheet of material 500 about in half. Then, as shown in FIGS. 5D and 5E, fold 544 bends side 502 back on itself to redouble a portion of the folded single sheet of material 500. Common bond line 526 maintains both of folds 542 and 544 in place to form lumens 503, 505.

Lumen 503 may be configured to receive a constrained implantable medical device, such as an endoprosthesis, and lumen 505 may be configured to receive at least one control feature, such as a deployment feature and/or a steering member. Lumen 505 is optionally shorted than lumen 503. Common bond line 526, which may, for example, represent a stich line or a thermal bond, may be generally parallel with a longitudinal axis of an endoprosthesis constrained within one of lumens 503, 505.

Figure 5F:
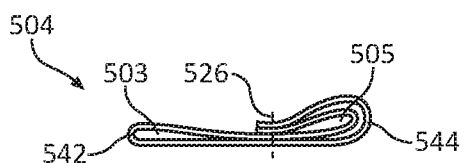

FIG. 5E illustrates a top view of endoprosthesis constraining sleeve 504, and FIG. 5F illustrates a side view of endoprosthesis constraining sleeve 504. As best illustrated in FIG. 5F, lumen 503 is formed from a single layer of the single sheet of material 500, whereas lumen 505 is formed from a double layer of the single sheet of material 500. The interior surfaces of lumen 503 are formed from side 501 of the single sheet of material 500, whereas the interior surfaces of lumen 503 are formed from side 502 of the single sheet of material 500. In other examples, the orientation of the single sheet of material 500 could be reversed such interior surfaces of lumen 503 are formed from side 502 of the single sheet of material 500, and the interior surfaces of lumen 503 are formed from side 501 of the single sheet of material 500.

FIGS. 6A-6E illustrate techniques for forming endoprosthesis constraining sleeve 604, which includes three lumens 603, 605, 607. Endoprosthesis constraining sleeve 604 is formed from a single sheet of material 600 (FIG. 6A) with three folds 642, 644, 646 and a common bond line 626. Endoprosthesis constraining sleeve 604 may be used as secondary sleeve 204 within delivery system 200, as the only constraining sleeve within another delivery system, or with any medical assembly in which it is useful to provide at least two adjacent lumens.

The single sheet of material 600 includes a first side 601 and a second side 602. In some examples, the single sheet of material 600 may include an exposed ePTFE layer on second side 602 with an exposed thermoplastic layer, such as an FEP layer on first side 601.

Figure 6A:
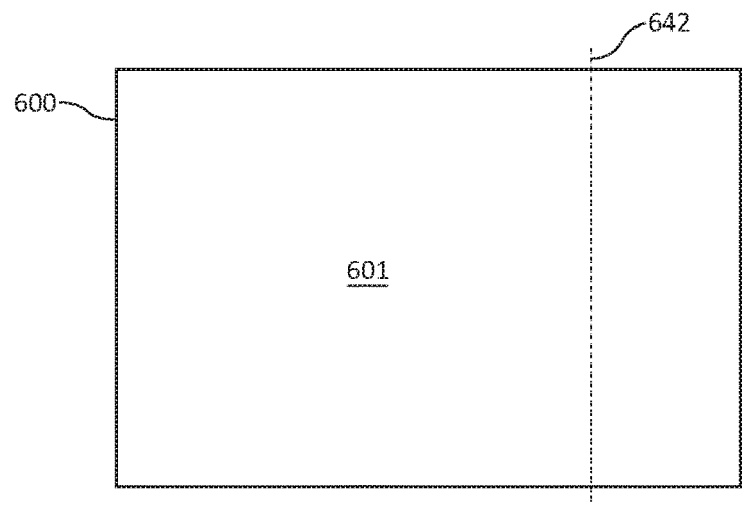
FIGS. 6A-6E illustrate example techniques for forming an endoprosthesis constraining sleeve including three lumens from a single sheet of material with three folds and a common bond line.
Figure 6B:
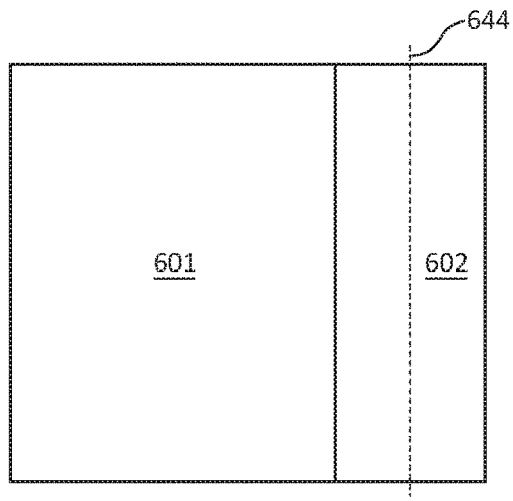
Figure 6C:
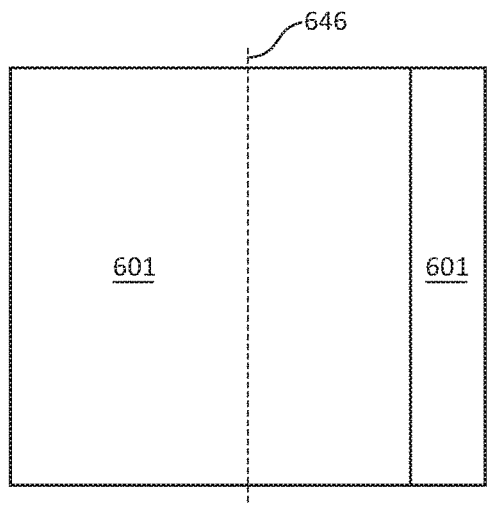
Figure 6D:
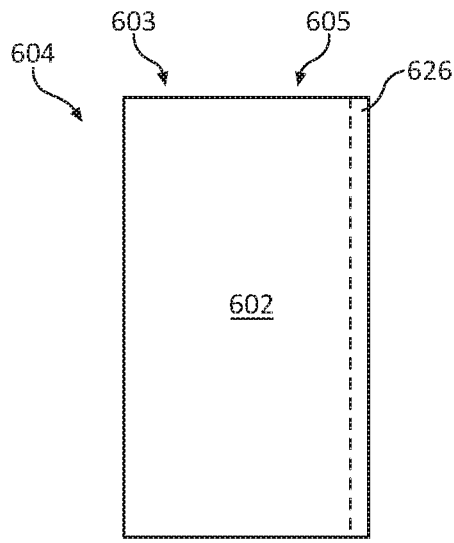

As shown in FIGS. 6B and 6C, to form endoprosthesis constraining sleeve 604, fold 642 bends a portion of side 601 back on itself. Then, as shown in FIGS. 6C and 6D, fold 644 bends side 602 back on itself to provide a three layered portion of the folded single sheet of material 600. Then fold 646 bends side 601 back on itself to cover the three layered portion and provide a four layered portion of the folded single sheet of material 600. Common bond line 626 maintains each of folds 642, 644, 646 in place to form lumens 603, 605, 607.

Lumen 603 may be configured to receive a constrained implantable medical device, such as an endoprosthesis, and lumen 605 may be configured to receive at least one control feature, such as a deployment feature and/or a steering member. In some examples, lumen 607 may not be used, but in other examples lumen 607 may also be configured to receive at least one control feature, such as a deployment feature and/or a steering member. Common bond line 626, which may, for example, represent a stich line or a thermal bond, may be generally parallel with a longitudinal axis of an endoprosthesis constrained within one of lumens 603, 605, 607.

Figure 6E:
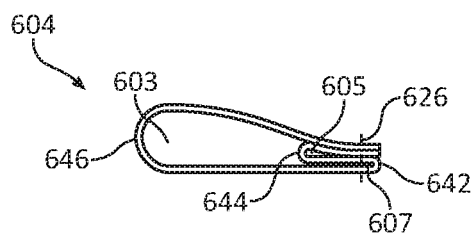

FIG. 6D illustrates a top view of endoprosthesis constraining sleeve 604, and FIG. 6E illustrates a side view of endoprosthesis constraining sleeve 604. As best illustrated in FIG. 6E, lumens 603 and 607 are each formed from a single layer of the single sheet of material 600, whereas lumen 605 is within lumen 603, and thus, formed from a double layer of the single sheet of material 600. The interior surfaces of lumens 603 and 607 are formed from side 601 of the single sheet of material 600, whereas the interior surfaces of lumen 603 are formed from side 602 of the single sheet of material 600. In other examples, the orientation of the single sheet of material 600 could be reversed such interior surfaces of lumens 603 and 607 are formed from side 602 of the single sheet of material 600, and the interior surfaces of lumen 603 are formed from side 601 of the single sheet of material 600.

Various modifications may be made to the disclosed examples within the spirit of this disclosure, especially in matters of structure, materials, elements, components, shape, size and arrangement of parts including combinations within the principles of the disclosure, to the full extent indicated by the broad, general meaning of the terms in which the appended claims are expressed. For example, while a variety of example configurations are provided, numerous additional configurations for endoprosthesis constraining sleeves including two lumens from a single sheet of material can readily be made within the spirit of this disclosure. To the extent that these various modifications and configurations do not depart from the spirit and scope of the appended claims, they are intended to be encompassed therein.

What is claimed is:

1. An endoprosthesis constraining sleeve comprising:
  a single sheet of material forming at least two folds and comprising a first side and a second side;
  a common bond line constraining the single sheet of material to maintain the at least two folds and to form at least two discrete lumens such that a portion of the first side of the single sheet is in contact with a portion of the second side of the single sheet,
  wherein a first lumen of the at least two lumens is configured to receive a constrained endoprosthesis therein, and
  wherein a second lumen of the at least two lumens is configured to receive a control feature therethrough.

2. The endoprosthesis constraining sleeve of claim 1, wherein the control feature includes one or more of a group consisting of:
  a deployment feature; and
  a steering member.

3. The endoprosthesis constraining sleeve of claim 1, wherein the common bond line includes at least one of:
  a thermal bond; and
  a stitch line.

4. The endoprosthesis constraining sleeve of claim 1, wherein the first lumen is formed from a single layer of the single sheet of material.

5. The endoprosthesis constraining sleeve of claim 4, wherein the second lumen is formed from two layers of the single sheet of material.

6. The endoprosthesis constraining sleeve of claim 4, wherein the second lumen is formed from the single layer of the single sheet of material.

7. The endoprosthesis constraining sleeve of claim 1,
wherein an interior surface of the first lumen is formed by the first side of the single sheet of material, and
wherein an interior surface of the second lumen is formed by the first side of the single sheet of material.

8. The endoprosthesis constraining sleeve of claim 1,
wherein an interior surface of the first lumen is formed by the first side of the single sheet of material, and
wherein an interior surface of the second lumen is formed by the second side of the single sheet of material.

9. The endoprosthesis constraining sleeve of claim 8, wherein the second lumen is formed from two layers of the single sheet of material.

10. The endoprosthesis constraining sleeve of claim 8, wherein the second lumen is within the first lumen.

11. The endoprosthesis constraining sleeve of claim 8,
wherein the first fold of the at least two bends the first side of the single sheet of material back on itself towards the common bond line to form the first lumen, and
wherein the second fold of the at least two bends the second side of the single sheet of material back on itself towards the common bond line to form the second lumen.

12. The endoprosthesis constraining sleeve of claim 1,
wherein the at least two folds includes at least three folds,
wherein the at least two discrete lumens includes at least three discrete lumens, and
wherein the common bond line constrains the single sheet of material to maintain the at least three folds and to form the at least three discrete lumens.

13. The device of claim 1, wherein the common bond line is generally parallel with a longitudinal axis of the constrained endoprosthesis.

14. The endoprosthesis constraining sleeve of claim 1, wherein the first lumen is configured to constrain the endoprosthesis to an intermediate configuration.

15. The endoprosthesis constraining sleeve of claim 1, wherein the single sheet of material is an expanded polytetrafluoroethylene (ePTFE) base layer.

16. The endoprosthesis constraining sleeve of claim 15, wherein a thermoplastic coating is applied to one of the first and second sides of the ePTFE base layer.

17. The endoprosthesis constraining sleeve of claim 1, wherein the single sheet of material is a fluorinated ethylene propylene (FEP) base layer.

18. The endoprosthesis constraining sleeve of claim 1, wherein the endoprosthesis is a stent graft.

* * * * *